United States Patent
Phillips

[11] Patent Number: 5,578,768
[45] Date of Patent: Nov. 26, 1996

[54] PLANKTON SAMPLE TAKING APPARATUS

[75] Inventor: William H. Phillips, Saginaw, Mich.

[73] Assignee: Trippensee Corporation, Saginaw, Mich.

[21] Appl. No.: 317,395

[22] Filed: Oct. 4, 1994

[51] Int. Cl.[6] .................................................... G01N 1/12
[52] U.S. Cl. ................................ 73/863.23; 73/863.52
[58] Field of Search ........................... 73/863.23, 863.24, 73/863.25, 864.51, 863.43, 863.52

[56] References Cited

U.S. PATENT DOCUMENTS

| | | | |
|---|---|---|---|
| 1,466,920 | 9/1923 | Anderson | 73/863.23 |
| 2,740,291 | 4/1956 | Brown | 73/863.25 X |
| 3,511,100 | 5/1970 | Vaughn et al. | 73/863.24 |
| 3,931,740 | 1/1976 | Carter | 73/863.23 |
| 4,055,087 | 10/1977 | Carle | 73/863.25 |
| 4,089,131 | 5/1978 | Phillips | 43/4 |
| 4,558,534 | 12/1985 | Phillips | 43/9 |
| 4,646,577 | 3/1987 | Phillips | 73/863.23 |
| 4,762,009 | 8/1988 | Scrudto | 73/863.23 |
| 5,404,761 | 4/1995 | Fellay et al. | 73/863.23 |

Primary Examiner—Thomas P. Noland
Attorney, Agent, or Firm—Learman & McCulloch

[57] ABSTRACT

A plankton sampler comprises a gathering net coupled to and in communication with a container having an inlet at one end and an outlet in its side through which water may flow outwardly of the container. Removably accommodated in the container is a screened sample collector, the screen of which is of such size in relation to that of the container that an annular space is provided between the collector screen and the inner surface of the container, thereby enabling water to flow outwardly from the collector into the annular space and thence through the opening in the side of the container.

14 Claims, 1 Drawing Sheet

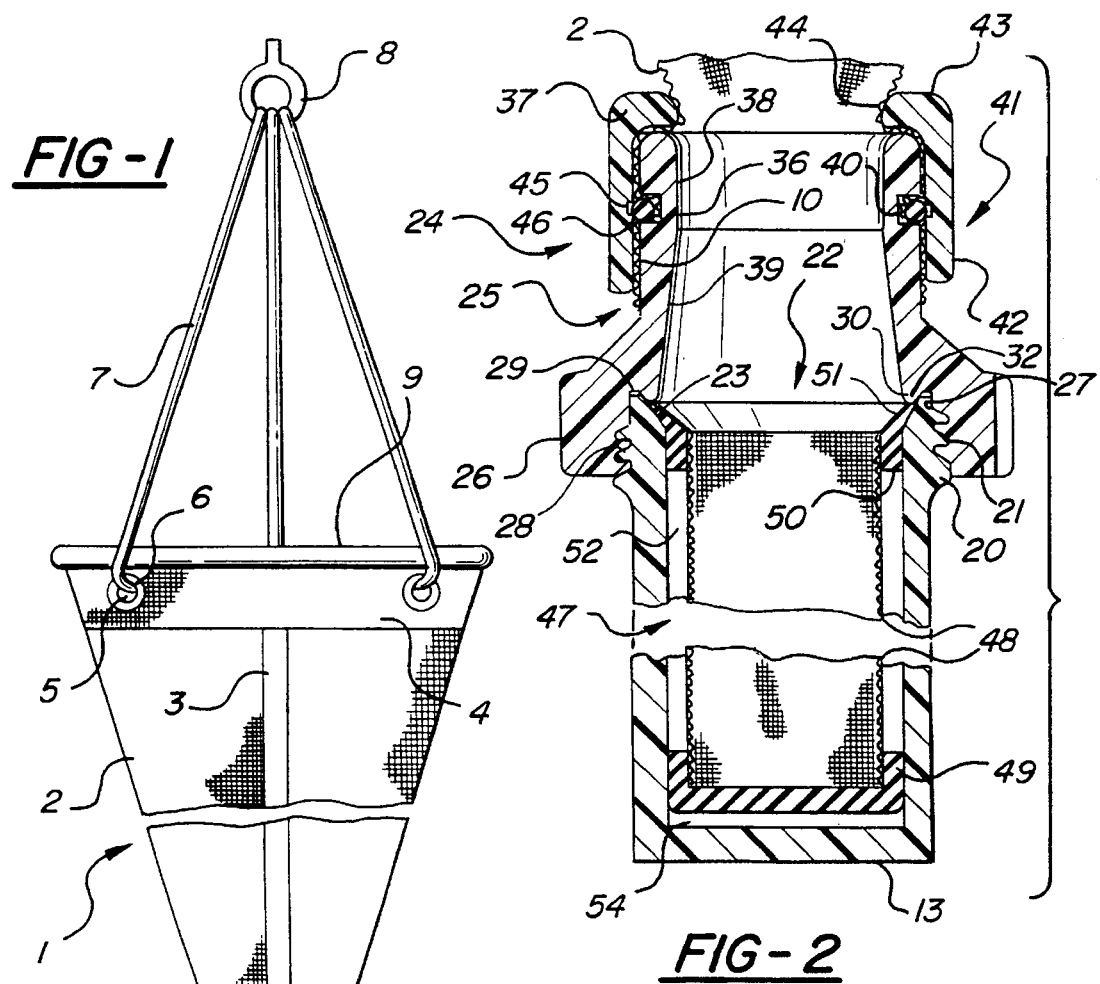
FIG-1
FIG-2
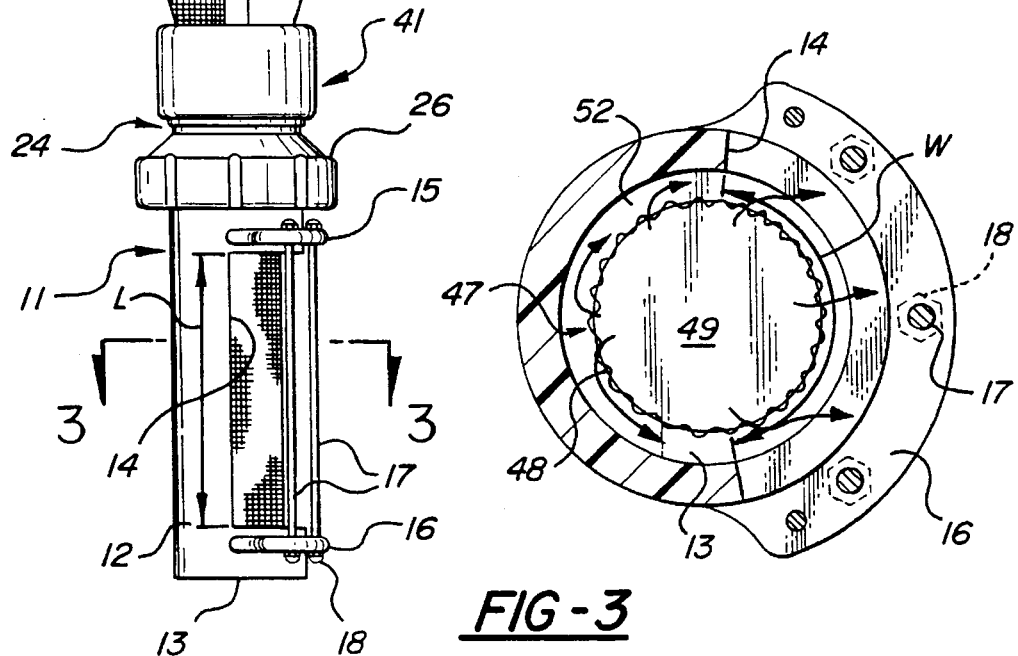
FIG-3

PLANKTON SAMPLE TAKING APPARATUS

This invention relates to apparatus adapted for use in the taking of plankton samples from a body of water.

BACKGROUND OF THE INVENTION

Plankton samples are taken from a body of water by moving sample taking apparatus through a body of water. Such apparatus conventionally comprises a conical net having its smaller end secured to the open end of a sample collector which has at least one screened opening therein, the screen having a mesh through which water may flow outwardly of the container, but which is small enough to prevent plankton from passing through the screen. Examples of the conventional apparatus are disclosed in Phillips U.S. Pat. Nos. 4,089,131; 4,558,534; and 4,646,577.

The apparatus disclosed in the above identified Phillips patents functions satisfactorily, but experience has revealed the desirability of improvements. For example, each of the patented devices has a sample collector having a water outlet opening which is covered by a screen. Any water admitted to the container must flow outwardly through the opening therein. In areas where the plankton population is large, it is not uncommon for the screen to become clogged fairly quickly, thereby inhibiting the flow of water outwardly of the container and minimizing the efficiency of the sample taking process.

The recovery of plankton collected by the prior art apparatus necessitates taking the apparatus out of service until such time as the plankton that has been collected is removed from the collector. This is because the screen by means of which the plankton is collected must be cleared of the plankton before the apparatus again can be used to take further samples.

A principal object of this invention is to overcome the disadvantages of the known plankton sampling apparatus.

SUMMARY OF THE INVENTION

Plankton sample taking apparatus constructed in accordance with the preferred embodiment of the invention comprises a container closed at one end and terminating at its other end in an inlet opening which may be coupled to the smaller diameter end of a conical gathering net in such manner that the net communicates directly with the interior of the container. The container has an annular wall provided with an outlet opening through which water that is introduced to the interior of the container may flow. The outlet opening has substantial height or length axially of the container and substantial circumferential width so as to provide free flow of water outwardly through the outlet opening. Overlying the outlet opening is a plurality of protective bars of relatively small diameter so as not to impede significantly the flow of water outwardly of the container.

Removably accommodated within the container is a plankton sample collector comprising a cylindrical screen having an open mouth at one end and a closure at its other end. The diameter of the screen portion of the collector is less than that of the container so that, when the collector is accommodated in the container, an annular space exists between the screen and the container wall. The mesh of the collector screen is sufficiently fine to permit water, but not plankton, to flow between the screen and the container.

The open end of the collector flares outwardly and is in sealed engagement with the open end of the container, thereby precluding the entry of water into the annular space via the inlet opening in the container.

THE DRAWINGS

The presently preferred embodiment of the invention is disclosed in the following description and in the accompanying drawings, wherein:

FIG. 1 is a side elevational view of a plankton sampler coupled to one end of a gathering net, the net being shown fragmentarily;

FIG. 2 is a fragmentary, vertical sectional view on an enlarged scale through the apparatus; and FIG. 3 is a sectional view taken on the line 3—3 of FIG. 1.

DETAILED DESCRIPTION

Apparatus constructed in accordance with the disclosed embodiment of the invention is adapted for use in conjunction with any one of a number of different kinds of conical sample gathering nets 1 having a tapering body 2 formed of nylon or other suitable netting material and equipped with axially extending reinforcing strips 3, as is conventional. At its larger diameter end the body 2 has a reinforcing band 4 of suitable material and is provided with openings 5, reinforced by suitable grommets 6, through which a towing bridle 7 passes. The bridle is connected to a ring 8 which may be attached to one end of a tow line. Preferably, a rigid hoop 9 is fitted to the larger diameter end of the body 2 so as to maintain that end of the body open. The smaller diameter end of the body 2 preferably includes a short, cylindrical neck portion or cod 10.

The net is adapted to be fitted to a cylindrical sample container 11 which, in the disclosed embodiment, comprises an annular wall 12 (defining a bore) having an inlet opening at one end. The container is closed at its other end by a bottom 13 and has a side, outlet opening 14 in its wall 12. The opening 14 has a length L constituting a substantial portion of the height of the wall 12 and is of substantial circumferential width, W, preferably between 90° and 180°. The opening 14 has an area considerably greater than that of the inlet opening. Obviously, more than one outlet opening can be provided in the container wall, but one usually is sufficient. In any case, each opening 14 is flanked at its upper and lower edges by projecting ribs 15 and 16 that are spanned by protective rods 17 which overlie the opening and are fixed in place by nuts 18.

At the open end of the container wall 12 is a flange 20 provided with an external thread 21. The container has a mouth 22 defined in part by a lip 23 having an outwardly inclined surface.

Apparatus for coupling the net 1 to the container 11 is designated generally by the reference character 24 and comprises an inner, annular body 25 at one end of which is an enlarged flange or skirt 26 having a bore 27 formed with a thread 28 which corresponds to the thread 21 on the container wall 12. The bore 27 terminates in an internal, radially extending shoulder 29 at the radially inner end of which is an annular, tapered bead 30 which extends axially and is radially spaced from the bore 27. The bead 30 has an inclined, radially outer surface 32 which confronts and nests with the lip 23 at the free end of the container mouth so as to form an interference sealing fit when the inner annular body 25 is screwed onto the container 11.

The inner body 25 also includes a generally cylindrical section 36 having an outer diameter corresponding substantially to that of the cod 10 of the net 1. The section 36 has a convex, smoothly rounded free end 37 and a cylindrical bore 38 which merges with a bore 39 that diverges in a direction toward the skirt 26 of the body 25 and communicates with the interior of the container 11. The section 36 of the body 25 also has an external, annular groove 40 therein.

The coupling apparatus 24 also includes an outer anchor ring 41 having an annular skirt 42 of such diameter as to accommodate the cylindrical section 36 of the coupling body 25. The anchor ring 41 terminates at one end in an annular flange 43 which overlies the end 37 of the coupling body 25 and has an outwardly convex surface 44. The skirt 42 also has an annular groove 45 in its inner surface and at a height to confront the groove 40. A rubbery, deformable retaining ring 46 is removably accommodated in the grooves 40 and 45 to retain the cod 10 between the parts 25 and 41.

Removably accommodated in the container 11 is a sample collector 47 comprising a cylindrical screen 48 having its lower end cemented or otherwise suitably secured to a cup-shaped closure 49 formed of suitable plastic or other material and its opposite end cemented or otherwise suitably secured to a ring 50 having an outwardly flared, tapering rim 51. The ring preferably is formed of deformable material such as polyurethane, so that the rim is flexible. The ring 50 provides communication with the interior of the net 1 via the cod 10 and the coupling apparatus 24.

The outside diameter of the ring 50 corresponds substantially to the inside diameter of the container wall 12, whereas the rim 51 is inclined at substantially the angle of the surface 23 of the flange 20. The rim 51 thus overlies and engages the lip 23. Preferably, the height of the rim 51 is such that its upper edge will be engaged by the bead 30 when the coupling member 25 is secured to the container 11, thereby causing the rim to be wedged into sealing engagement with the lip 23.

Although the outside diameter of the mounting ring 50 corresponds substantially to the inside diameter of the container wall 12, the diameter of the screen 48 is less than the bore of the container, i.e., the inside diameter of the container wall, thereby providing an annular space 52 of substantially uniform width between the inner surface of the wall 12 and the screen 48. Preferably, the overall height of the screened collector 47 is less than that of the container 11, thereby providing a clearance 54 between the closure 49 and the container bottom 13. The provision of the clearance ensures that the forming of a seal between the mounting ring rim 51 and the upper end of the body 11 will not be precluded by engagement of the closure 49 with the bottom 13 of the container.

The screen 48 may be formed of metal or synthetic material, but in any event the mesh should be sufficiently large to enable water to flow through the screen, but prevent the flow of plankton through the screen.

When the screened collector 47 is accommodated in the container 11 and the apparatus is moved through a body of water, water and plankton will enter the screened collector 47 through the net 1 and the coupling apparatus 24. Water entering the screened collector 47 will pass through the screen 48 into the annular space 52 and through the opening 14 in the container wall 12. Plankton will be retained on the inner surface of the screen.

The presence of the annular space 52 will enable water to flow through the screen 48 throughout the length thereof, thereby enabling plankton to be deposited on the interior of the screen throughout its circumference and height. Accordingly, the screen will not become clogged with plankton nearly as quickly as would be the case if all of the plankton were collected on a screen covering the opening 14.

Whenever a sufficient quantity of plankton has been collected inside the screened collector, or upon the passage of a predetermined period of time, the apparatus may be withdrawn from the body of water, the coupling 25 disconnected from the container 11, and the collector 47 removed from the container. All of the collected plankton will be contained within the collector, rather than in the container. Accordingly, a fresh screened collector 47 may be accommodated in the container, the parts reassembled, and further sampling conducted without having to wait for removal of the collected plankton from the collector.

The disclosed embodiment is representative of a presently preferred form of the invention, but is intended to be illustrative rather than definitive thereof. The invention is defined in the claims.

I claim:

1. Apparatus for taking a sample from a body of water comprising an elongate container having a wall defining a bore of selected transverse dimension, said container having an inlet and an outlet; means for coupling said inlet to a sample gathering device; and a hollow, tubular sample collector accommodated within said bore, said collector having a transverse dimension less than that of said bore thereby to provide a space between said collector and the wall defining said bore, said collector having a screened portion in communication with said inlet and through which water may flow into said space for discharge through said outlet.

2. Apparatus according to claim 1 wherein said inlet is at one end of said container and said outlet is at a side of said container and between said one end and an end opposite said one end.

3. Apparatus according to claim 1 wherein said container has protective rods overlying said outlet.

4. Apparatus according to claim 1 wherein said bore and said collector are cylindrical.

5. Apparatus according to claim 4 wherein said collector is open at one end thereof for communicating with said inlet and closed at an opposite end thereof.

6. Apparatus according to claim 5 wherein said container has a bottom and said collector has a length less than that of said container, whereby the opposite end of said collector is spaced from the bottom of said container.

7. Apparatus according to claim 4 wherein said screen portion of said collector is substantially centered with respect to the bore of said container thereby providing a substantially uniform, annular space between said screen portion and the wall defining said bore.

8. Apparatus for taking a sample from a body of water comprising a hollow container having an annular wall, an inlet at one end, a bottom at an opposite end, and an outlet; an annular sample collector removably accommodated in said container and having an opening at one end in communication with the inlet of said container and a closure at an opposite end, said collector having a screen portion between its ends; means for coupling said one end of said container to a sample gathering device; and means for removably securing said one end of said collector to said one end of said container in communication with said device, said screen portion of said collector having a diameter less than that of said container wall thereby providing an annular space between said screen portion and said container wall.

9. Apparatus according to claim 8 wherein said space forms an annulus of substantially uniform width.

10. Apparatus according to claim 8 wherein said collector has a length less than that of said container thereby providing a space between said closure and said bottom.

11. Apparatus according to claim 8 including spaced apart, protective rods carried by said container and overlying said outlet.

12. Apparatus according to claim 8 including seal means reacting between said container and said collector at said inlet to prevent the flow of water into said annular space except through said screen portion of said collector.

13. Apparatus according to claim 8 wherein said outlet has an area greater than that of said inlet.

14. Apparatus according to claim 13 wherein said outlet is in said wall of said container and extends between 90° and 180° circumferentially of said container.

\* \* \* \* \*